US012265196B2

(12) United States Patent
Sayed et al.

(10) Patent No.: US 12,265,196 B2
(45) Date of Patent: Apr. 1, 2025

(54) AUTOMATIC LANDING OF FORMATION TESTING TOOLS

(71) Applicant: Halliburton Energy Services, Inc., Houston, TX (US)

(72) Inventors: Sadeed Sayed, Singapore (SG); Ahmed Fouda, Houston, TX (US); Bin Dai, Katy, TX (US); Christopher Michael Jones, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 296 days.

(21) Appl. No.: 17/977,994

(22) Filed: Oct. 31, 2022

(65) Prior Publication Data
US 2024/0142657 A1    May 2, 2024

(51) Int. Cl.
*G01V 5/04* (2006.01)
*E21B 47/04* (2012.01)
*E21B 49/08* (2006.01)
*G01N 33/28* (2006.01)

(52) U.S. Cl.
CPC ............. *G01V 5/04* (2013.01); *E21B 47/04* (2013.01); *E21B 49/081* (2013.01); *G01N 33/2823* (2013.01)

(58) Field of Classification Search
CPC ......... G01V 5/04; E21B 47/04; E21B 49/081; G01N 33/2823
See application file for complete search history.

(56) References Cited

U.S. PATENT DOCUMENTS

| 9,638,034 | B2 | 5/2017 | Chen et al. |
| 9,798,035 | B2 | 10/2017 | Fouda et al. |
| 9,964,659 | B2 | 5/2018 | Fouda et al. |
| 10,301,935 | B2 | 5/2019 | Wang et al. |
| 10,329,908 | B2 | 6/2019 | Fox et al. |
| 10,392,932 | B2 | 8/2019 | Wilson et al. |
| 10,422,913 | B2 | 9/2019 | Fouda et al. |
| 10,816,689 | B2 | 10/2020 | Fouda et al. |

(Continued)

FOREIGN PATENT DOCUMENTS

WO    2016159997 A1    10/2016

OTHER PUBLICATIONS

International Search Report and Written Opinion for International Patent Application No. PCT/US2022/050279 dated Jul. 20, 2023.

(Continued)

*Primary Examiner* — David P Porta
*Assistant Examiner* — Gisselle M Gutierrez
(74) *Attorney, Agent, or Firm* — Benjamin Ford; C. Tumey Law Group PLLC

(57) ABSTRACT

A method and system for correlating two or more logs. The method may include reviewing an openhole log to identify one or more depths within a wellbore for testing, disposing a fluid sampling tool into the wellbore, creating a correlation log with the fluid sampling tool, depth-matching the correlation log to the openhole log to create a relative shift table, and moving the fluid sampling tool to the one or more depths within the wellbore based at least in part on the relative shift table. The system may include a fluid sampling tool disposed in a wellbore to create a correlation log and an information handling system connected to the fluid sampling tool.

20 Claims, 10 Drawing Sheets

(56) References Cited

U.S. PATENT DOCUMENTS

| | | |
|---|---|---|
| 10,901,115 B2 | 1/2021 | Kirkwood et al. |
| 10,920,578 B2 | 2/2021 | San Martin et al. |
| 11,008,853 B2 | 5/2021 | Jones et al. |
| 11,143,779 B2 | 10/2021 | Ewe et al. |
| 11,199,643 B2 | 12/2021 | Samson et al. |
| 11,280,929 B2 | 3/2022 | Donderici et al. |
| 2007/0061079 A1* | 3/2007 | Hu ................ E21B 25/00 702/6 |
| 2015/0241591 A1* | 8/2015 | Burmester ........... G01V 11/00 702/7 |
| 2016/0327678 A1 | 11/2016 | Benson et al. |
| 2016/0341834 A1 | 11/2016 | Bartetzko et al. |
| 2018/0017697 A1 | 1/2018 | Fouda et al. |
| 2018/0187543 A1 | 7/2018 | Wilson et al. |
| 2018/0216458 A1* | 8/2018 | Garcia ................ E21B 49/10 |
| 2018/0252100 A1 | 9/2018 | Ranjan et al. |
| 2018/0348398 A1* | 12/2018 | Wlodarczyk ........... G01V 1/48 |
| 2019/0196039 A1 | 6/2019 | Wilson et al. |
| 2020/0149387 A1 | 5/2020 | Stark et al. |
| 2021/0183009 A1 | 6/2021 | Fouda |
| 2021/0304386 A1 | 9/2021 | Guner et al. |
| 2022/0106871 A1* | 4/2022 | Al Ibrahim ............. G01V 3/30 |
| 2022/0178244 A1 | 6/2022 | Fouda et al. |
| 2022/0178245 A1 | 6/2022 | Fouda et al. |

OTHER PUBLICATIONS

Dai, Bin, et al. "Auto-Navigation of Optimal Formation Pressure Testing Locations by Machine Learning Methods." SPWLA 60th Annual Logging Symposium. OnePetro, 2019.

Le, Thai, et al. "A Machine-Learning Framework for Automating Well-Log Depth Matching." Petrophysics—The SPWLA Journal of Formation Evaluation and Reservoir Description 60.05 (2019): 585-595.

Umeonaku, Loretta, et al. "Realtime Aaquisition of Formation Pressure Data for Reservoir Characterization and Safe Drilling." SPE Nigeria Annual International Conference and Exhibition. OnePetro, 2019.

Torres Caceres, Veronica Alejandra, et al. "Automated Log Data Analytics Workflow—The Value of Data Access and Management to Reduced Turnaround Time for Log Analysis." Petrophysics—The SPWLA Journal of Formation Evaluation and Reservoir Description 63.01 (2022): 35-60.

* cited by examiner

AUTOMATIC LANDING OF FORMATION TESTING TOOLS

BACKGROUND

During oil and gas exploration, many types of information may be collected and analyzed. The information may be used to determine the quantity and quality of hydrocarbons in a reservoir and to develop or modify strategies for hydrocarbon production. For instance, the information may be used for reservoir evaluation, flow assurance, reservoir stimulation, facility enhancement, production enhancement strategies, and reserve estimation. One technique for collecting relevant information involves pressure testing a reservoir of interest at any specified depth. There are a variety of different tools that may be used to perform the pressure test to determine formation parameters at a specified depth.

Formation pressure testing provides important information for exploration and production activities. Accurate reservoir pressure measurements are necessary to ensure a well is drilled safely, and to identify and evaluate the potential and value of that discovery. Interpretation of pressure gradients provide the reservoir compartmentalization structure of a well, oil-gas-water fluid contacts, and are indicative of compositional grading, as evidenced by second order pressure change over depth. It is believed that pressure testing quality is sufficient for high resolution analysis. Unfortunately, obtaining quality data from formation testing is difficult and prolonged. Locations initially selected for formation pretesting along the wellbore are often not optimal, and the time spent conducting pressure testing on those locations is wasted. In a conventional formation test program, a basic depth matching is conducted to match the gamma readings from the formation tester with the gammy reading from openhole logs. However, even after the basic depth matching, the location where a formation sampling tool may land may still be off the location picked from the openhole log up to a few feet due to the uncertainty of depth matching.

BRIEF DESCRIPTION OF THE DRAWINGS

These drawings illustrate certain aspects of some of the embodiments of the present disclosure, and should not be used to limit or define the disclosure.

DETAILED DESCRIPTION

Disclosed below are methods and systems for downhole pressure testing. Specifically, method and systems for landing a formation sampling tool at one or more chooses depths within a wellbore. This may be performed using a machine learning system and method to correlate the pretest quality and conventional openhole logs (Gamma ray, density, porosity, resistivity, NMR, acoustic, etc.) based on a database, which contains both openhole logs (significant features) and pretest quality index (targets). Once the model is trained and validated, it may guide personnel to select depth locations within a wellbore to conduct pressure tests based on openhole logs. Additionally, the machine learning system may enable the fluid sampling tool to precisely land on the depth or depths chosen for a pressure test.

Figure 1:
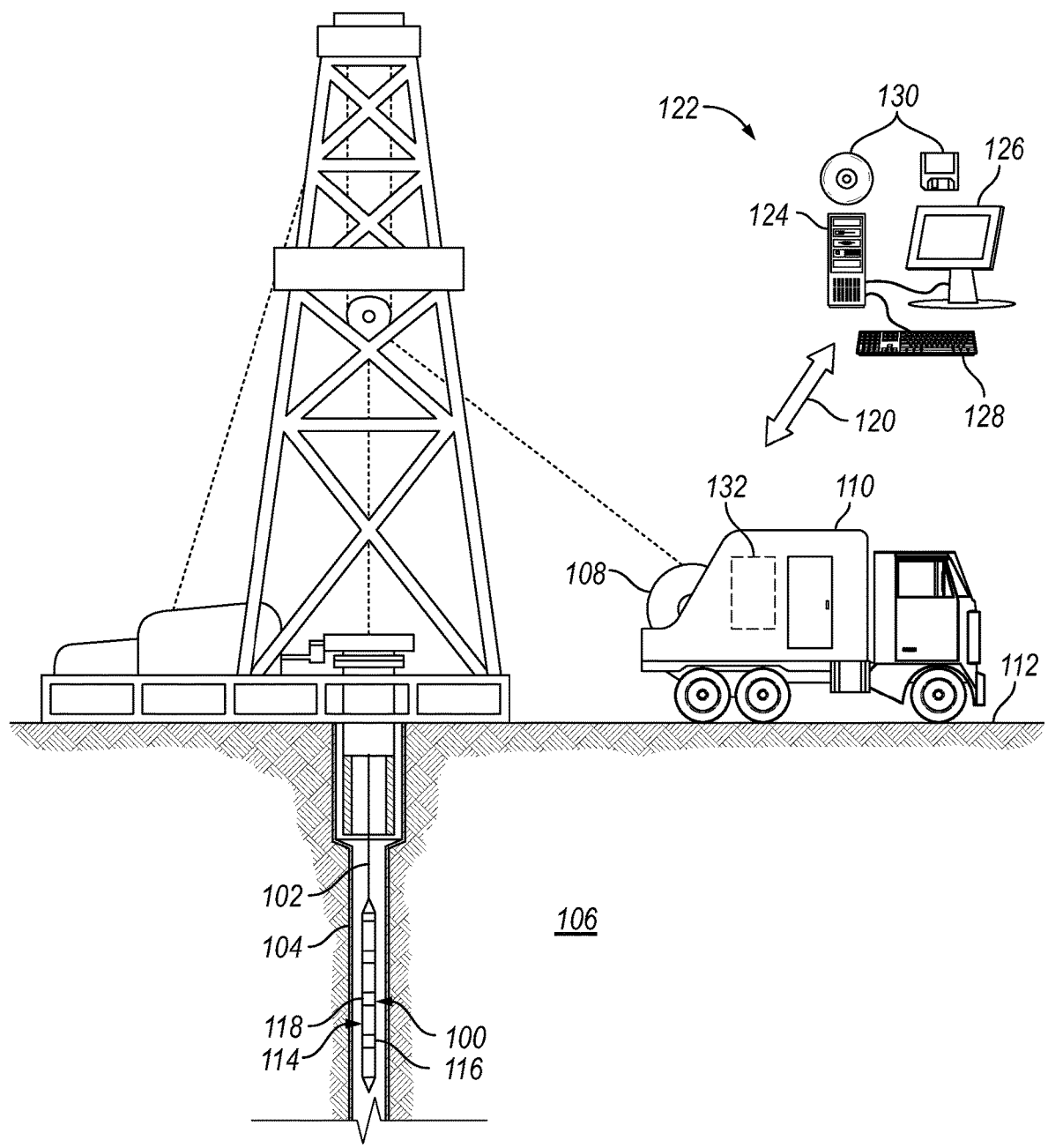
FIG. 1 is a schematic diagram of an example a fluid sampling tool on a wireline.

FIG. 1 is a schematic diagram of fluid sampling tool 100 on a conveyance 102. As illustrated, wellbore 104 may extend through subterranean formation 106. In examples, reservoir fluid may be contaminated with well fluid (e.g., drilling fluid) from wellbore 104. As described herein, the fluid sample may be analyzed to determine fluid contamination and other fluid properties of the reservoir fluid. As illustrated, a wellbore 104 may extend through subterranean formation 106. While the wellbore 104 is shown extending generally vertically into the subterranean formation 106, the principles described herein are also applicable to wellbores that extend at an angle through the subterranean formation 106, such as horizontal and slanted wellbores. For example, although FIG. 1 shows a vertical or low inclination angle well, high inclination angle or horizontal placement of the well and equipment is also possible. It should further be noted that while FIG. 1 generally depicts a land-based operation, those skilled in the art will readily recognize that the principles described herein are equally applicable to subsea operations that employ floating or sea-based platforms and rigs, without departing from the scope of the disclosure.

As illustrated, a hoist 108 may be used to run fluid sampling tool 100 into wellbore 104. Hoist 108 may be disposed on a vehicle 110. Hoist 108 may be used, for example, to raise and lower conveyance 102 in wellbore 104. While hoist 108 is shown on vehicle 110, it should be understood that conveyance 102 may alternatively be disposed from a hoist 108 that is installed at surface 112 instead of being located on vehicle 110. Fluid sampling tool 100 may be suspended in wellbore 104 on conveyance 102. Other conveyance types may be used for conveying fluid sampling tool 100 into wellbore 104, including coiled tubing and wired drill pipe, conventional drill pipe for example. Fluid sampling tool 100 may comprise a tool body 114, which may be elongated as shown on FIG. 1. Tool body 114 may be any suitable material, including without limitation titanium, stainless steel, alloys, plastic, combinations thereof, and the like. Fluid sampling tool 100 may further include one or more sensors 116 for measuring properties of the fluid sample, reservoir fluid, wellbore 104, subterranean formation 106, or the like. In examples, fluid sampling tool 100 may also include a fluid analysis module 118, which may be operable to process information regarding fluid sample, as described below. The fluid sampling tool 100 may be used to collect fluid samples from subterranean formation

106 and may obtain and separately store different fluid samples from subterranean formation 106.

In examples, fluid analysis module 118 may comprise at least one a sensor that may continuously monitor a reservoir fluid. Such sensors include optical sensors, acoustic sensors, electromagnetic sensors, conductivity sensors, resistivity sensors, a capacitance sensor, selective electrodes, density sensors, mass sensors, thermal sensors, chromatography sensors, viscosity sensors, bubble point sensors, fluid compressibility sensors, flow rate sensors. Sensors may measure a contrast between drilling fluid filtrate properties and formation fluid properties. Fluid analysis module 118 may be operable to derive properties and characterize the fluid sample. By way of example, fluid analysis module 118 may measure absorption, transmittance, or reflectance spectra and translate such measurements into component concentrations of the fluid sample, which may be lumped component concentrations, as described above. The fluid analysis module 118 may also measure gas-to-oil ratio, fluid composition, water cut, live fluid density, live fluid viscosity, formation pressure, and formation temperature. Fluid analysis module 118 may also be operable to determine fluid contamination of the fluid sample and may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, fluid analysis module 118 may include random access memory (RAM), one or more processing units, such as a central processing unit (CPU), or hardware or software control logic, ROM, and/or other types of nonvolatile memory.

Any suitable technique may be used for transmitting phase signals from the fluid sampling tool 100 to the surface 112. As illustrated, a communication link 120 (which may be wired or wireless, for example) may be provided that may transmit data from fluid sampling tool 100 to an information handling system 122 at surface 112. Information handling system 122 may include a processing unit 124, a monitor 126, an input device 128 (e.g., keyboard, mouse, etc.), and/or computer media 130 (e.g., optical disks, magnetic disks) that can store code representative of the methods described herein. The information handling system 122 may act as a data acquisition system and possibly a data processing system that analyzes information from fluid sampling tool 100. For example, information handling system 122 may process the information from fluid sampling tool 100 for determination of fluid contamination. The information handling system 122 may also determine additional properties of the fluid sample (or reservoir fluid), such as component concentrations, pressure-volume-temperature properties (e.g., bubble point, phase envelop prediction, etc.) based on the fluid characterization. This processing may occur at surface 112 in real-time. Alternatively, the processing may occur downhole hole or at surface 112 or another location after recovery of fluid sampling tool 100 from wellbore 104. Alternatively, the processing may be performed by an information handling system in wellbore 104, such as fluid analysis module 118. The resultant fluid contamination and fluid properties may then be transmitted to surface 112, for example, in real-time.

Figure 2:
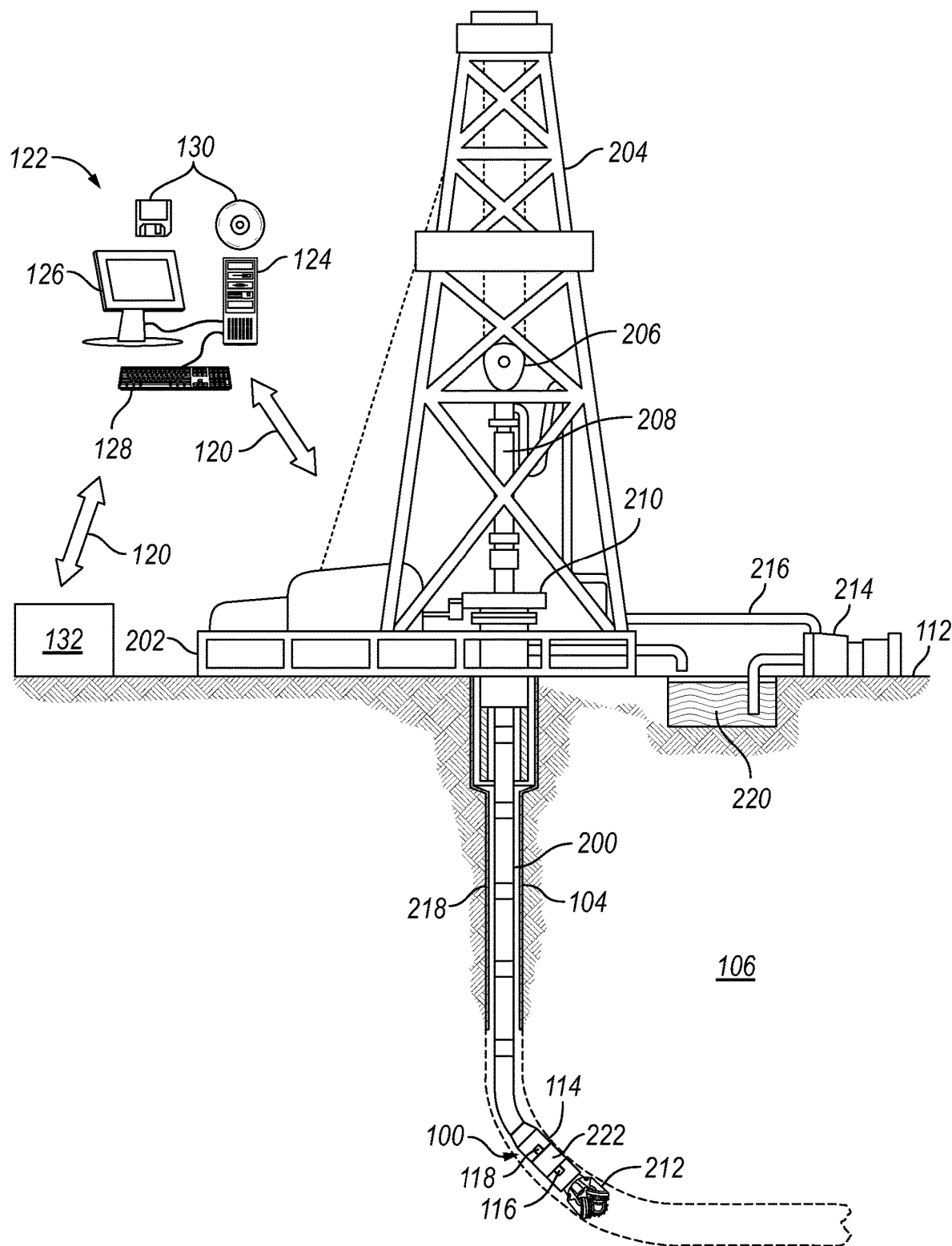
FIG. 2 is a schematic diagram of an example the fluid sampling tool on a drill string.

Referring now to FIG. 2, a schematic diagram of fluid sampling tool 100 disposed on a drill string 200 in a drilling operation. Fluid sampling tool 100 may be used to obtain a fluid sample, for example, a fluid sample of a reservoir fluid from subterranean formation 106. The reservoir fluid may be contaminated with well fluid (e.g., drilling fluid) from wellbore 104. As described herein, the fluid sample may be analyzed to determine fluid contamination and other fluid properties of the reservoir fluid. As illustrated, a wellbore 104 may extend through subterranean formation 106. While the wellbore 104 is shown extending generally vertically into the subterranean formation 106, the principles described herein are also applicable to wellbores that extend at an angle through the subterranean formation 106, such as horizontal and slanted wellbores. For example, although FIG. 2 shows a vertical or low inclination angle well, high inclination angle or horizontal placement of the well and equipment is also possible. It should further be noted that while FIG. 2 generally depicts a land-based operation, those skilled in the art will readily recognize that the principles described herein are equally applicable to subsea operations that employ floating or sea-based platforms and rigs, without departing from the scope of the disclosure.

As illustrated, a drilling platform 202 may support a derrick 204 having a traveling block 206 for raising and lowering drill string 200. Drill string 200 may include, but is not limited to, drill pipe and coiled tubing, as generally known to those skilled in the art. A kelly 208 may support drill string 200 as it may be lowered through a rotary table 210. A drill bit 212 may be attached to the distal end of drill string 200 and may be driven either by a downhole motor and/or via rotation of drill string 200 from the surface 112. Without limitation, drill bit 212 may comprise, roller cone bits, PDC bits, natural diamond bits, any hole openers, reamers, coring bits, and the like. As drill bit 212 rotates, it may create and extend wellbore 104 that penetrates various subterranean formations 106. A pump 214 may circulate drilling fluid through a feed pipe 216 to kelly 208, downhole through interior of drill string 200, through orifices in drill bit 212, back to surface 112 via annulus 218 surrounding drill string 200, and into a retention pit 220.

Drill bit 212 may be just one piece of a downhole assembly that may include one or more drill collars 222 and fluid sampling tool 100. Fluid sampling tool 100, which may be built into the drill collars 222 may gather measurements and fluid samples as described herein. One or more of the drill collars 222 may form a tool body 114, which may be elongated as shown on FIG. 2. Tool body 114 may be any suitable material, including without limitation titanium, stainless steel, alloys, plastic, combinations thereof, and the like. Fluid sampling tool 100 may be similar in configuration and operation to fluid sampling tool 100 shown on FIG. 1 except that FIG. 2 shows fluid sampling tool 100 disposed on drill string 200. Alternatively, the sampling tool may be lowered into the wellbore after drilling operations on a wireline.

Fluid sampling tool 100 may further include one or more sensors 116 for measuring properties of the fluid sample reservoir fluid, wellbore 104, subterranean formation 106, or the like. The properties of the fluid are measured as the fluid passes from the formation through the tool and into either the wellbore or a sample container. As fluid is flushed in the near wellbore region by the mechanical pump, the fluid that passes through the tool generally reduces in drilling fluid filtrate content, and generally increases in formation fluid content. The fluid sampling tool 100 may be used to collect a fluid sample from subterranean formation 106 when the filtrate content has been determined to be sufficiently low. Sufficiently low depends on the purpose of sampling. For some laboratory testing below 10% drilling fluid contamination is sufficiently low, and for other testing below 1% drilling fluid filtrate contamination is sufficiently low. Sufficiently low also depends on the nature of the formation fluid such that lower requirements are generally needed, the lighter the oil as designated with either a higher GOR or a higher API gravity. Sufficiently low also depends on the rate of cleanup in a cost benefit analysis since longer pumpout times utilized to incrementally reduce the contamination levels may have prohibitively large costs. As previously described, the fluid sample may comprise a reservoir fluid, which may be contaminated with a drilling fluid or drilling fluid filtrate. Fluid sampling tool 100 may obtain and separately store different fluid samples from subterranean formation 106 with fluid analysis module 118. Fluid analysis module 118 may operate and function in the same manner as described above. However, storing of the fluid samples in the fluid sampling tool 100 may be based on the determination of the fluid contamination. For example, if the fluid contamination exceeds a tolerance, then the fluid sample may not be stored. If the fluid contamination is within a tolerance, then the fluid sample may be stored in fluid sampling tool 100.

As previously described, information from fluid sampling tool 100 may be transmitted to an information handling system 122, which may be located at surface 112. As illustrated, communication link 120 (which may be wired or wireless, for example) may be provided that may transmit data from fluid sampling tool 100 to an information handling system 111 at surface 112. Information handling system 140 may include a processing unit 124, a monitor 126, an input device 128 (e.g., keyboard, mouse, etc.), and/or computer media 130 (e.g., optical disks, magnetic disks) that may store code representative of the methods described herein. In addition to, or in place of processing at surface 112, processing may occur downhole (e.g., fluid analysis module 118). In examples, information handling system 122 may perform computations to estimate clean fluid composition.

Figure 3:
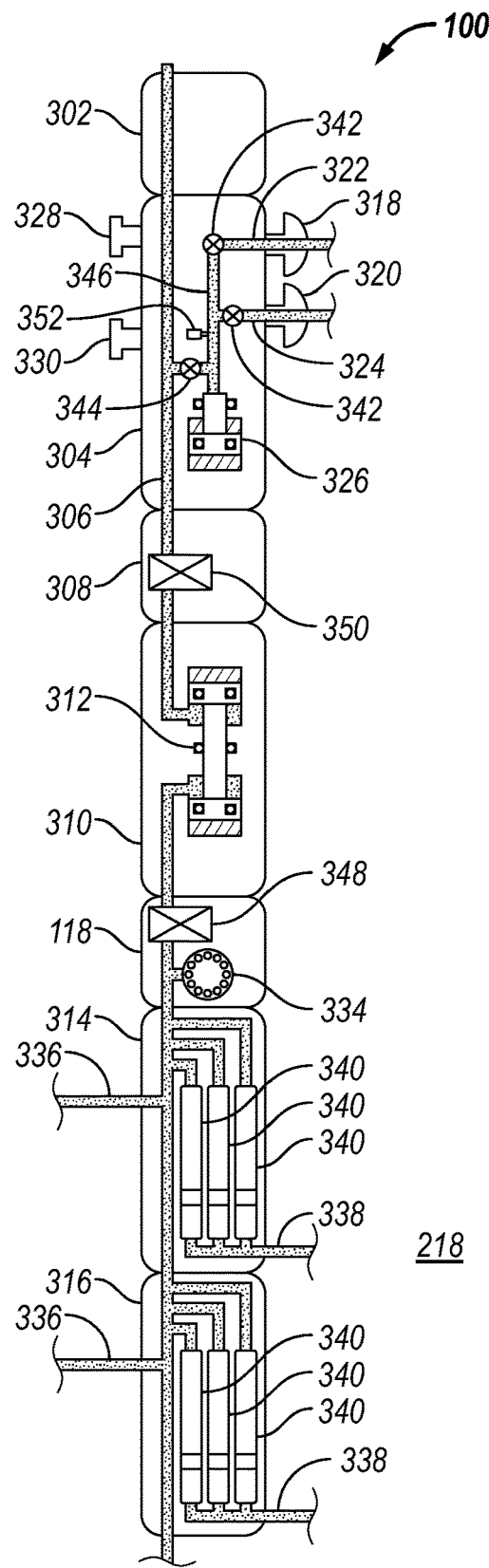
FIG. 3 is a schematic of the fluid sampling tool.

FIG. 3 is a schematic of fluid sampling tool 100. In examples one embodiment, the fluid sampling tool 100 includes a power telemetry section 302 through which the tool communicates with other actuators and sensors 116 in drill string 200 or conveyance 102 (e.g., referring to FIGS. 1 and 2), the drill string's telemetry section 302, and/or directly with a surface telemetry system (not illustrated). In examples, power telemetry section 302 may also be a port through which the various actuators (e.g., valves) and sensors (e.g., temperature and pressure sensors) in the fluid sampling tool 100 may be controlled and monitored. In examples, power telemetry section 302 includes a computer that exercises the control and monitoring function. In one embodiment, the control and monitoring function is performed by a computer in another part of the drill string or wireline tool (not shown) or by information handling system 122 on surface 112 (e.g., referring to FIGS. 1 and 2).

In examples, fluid sampling tool 100 includes a dual probe section 304, which extracts fluid from the reservoir and delivers it to a passageway 306 that extends from one end of fluid sampling tool 100 to the other. Without limitation, dual probe section 304 includes two probes 318, 320 which may extend from fluid sampling tool 100 and press against the inner wall of wellbore 104 (e.g., referring to FIG. 1). Probe channels 322, 324 may connect probes 318, 320 to passageway 306. The high-volume bidirectional pump 312 may be used to pump fluids from the reservoir, through probe channels 322, 324 and to passageway 306. Alternatively, a low volume pump 326 may be used for this purpose. Two standoffs or stabilizers 328, 330 hold fluid sampling tool 100 in place as probes 318, 320 press against the wall of wellbore 104. In examples, probes 318, 320 and stabilizers 328, 330 may be retracted when fluid sampling tool 100 may be in motion and probes 318, 320 and stabilizers 328, 330 may be extended to sample the formation fluids at any suitable location in wellbore 104. Other probe sections include focused sampling probes, oval probes, or packers.

In examples, passageway 306 may be connected to other tools disposed on drill string 200 or conveyance 102 (e.g., referring to FIGS. 1 and 2). In examples, fluid sampling tool 100 may also include a quartz gauge section 308, which may include sensors to allow measurement of properties, such as temperature and pressure, of fluid in passageway 306. Additionally, fluid sampling tool 100 may include a flow-control pump-out section 310, which may include a high-volume bidirectional pump 312 for pumping fluid through passageway 306. In examples, fluid sampling tool 100 may include two multi-chamber sections 314, 316, referred to collectively as multi-chamber sections 314, 316 or individually as first multi-chamber section 314 and second multi-chamber section 316, respectively.

In examples, multi-chamber sections 314, 316 may be separated from flow-control pump-out section 310 by sensor section 332, which may house at least one non-optical fluid sensor 348, 350 and/or at least optical measurement tool 334. It should be noted that non-optical fluid sensor 348, 350 and optical measurement tool 334 may be disposed in any order on passageway 306. Additionally, although depicted in sensor section 332. Both non-optical fluid sensor 348, 350 and optical measurement tool 334 may be disposed along passageway 306 at any suitable location within fluid sampling tool 100.

Non-optical fluid sensor 348, 350 may be displaced within sensor section 332 in-line with passageway 306 to be a "flow through" sensor. In alternate examples, non-optical fluid sensor 348, 350 may be connected to passageway 306 via an offshoot of passageway 306. Without limitation, optical measurement tool 334 may include but not limited to the density sensor, capacitance sensor, resistivity sensor, and/or combinations thereof. In examples, non-optical fluid sensor 348, 350 may operate and/or function to measure fluid properties of drilling fluid filtrate.

Optical measurement tool 334 may be displaced within sensor section 332 in-line with passageway 306 to be a "flow through" sensor. In alternate examples, optical measurement tool 334 may be connected to passageway 306 via an offshoot of passageway 306. Without limitation, optical measurement tool 334 may include optical sensors, acoustic sensors, electromagnetic sensors, conductivity sensors, resistivity sensors, a capacitance sensor, selective electrodes, density sensors, mass sensors, thermal sensors, chromatography sensors, viscosity sensors, bubble point sensors, fluid compressibility sensors, flow rate sensors, microfluidic sensors, selective electrodes such as ion selective electrodes, and/or combinations thereof. In examples, optical measurement tool 334 may operate and/or function to measure drilling fluid filtrate, discussed further below.

Additionally, multi-chamber section 314, 316 may comprise access channel 336 and chamber access channel 338. Without limitation, access channel 336 and chamber access channel 338 may operate and function to either allow a solids-containing fluid (e.g., mud) disposed in wellbore 104 in or provide a path for removing fluid from fluid sampling tool 100 into wellbore 104. As illustrated, multi-chamber section 314, 316 may comprise a plurality of chambers 340. Chambers 340 may be sampling chamber that may be used to sample wellbore fluids, formation fluids, and/or the like during measurement operations.

During downhole measurement operations, a pumpout operation may be performed. A pumpout may be an operation where at least a portion of a fluid which may contain solids—(e.g., drilling fluid, mud, filtrate etc.) may move through fluid sampling tool 100 until substantially increasing concentrations of formation fluids enter fluid sampling tool 100. For example, during pumpout operations, probes 318, 320 may be pressed against the inner wall of wellbore 104 (e.g., referring to FIG. 1). Pressure may increase at probes 318, 320 due to compression against the formation 106 (e.g., referring to FIG. 1 or 2) exerting pressure on probes 318, 320. As pressure rises and reaches a predetermined pressure, valves 342 opens so as to close equalizer valve 344, thereby isolating fluid passageway 346 from annulus 218. In this manner, valve 342 ensures that equalizer valve 344 closes only after probes 318, 320 has entered contact with mud cake (not illustrated) that is disposed against the inner wall of wellbore 104. In examples, as probes 318, 320 are pressed against the inner wall of wellbore 104, the pressure rises and closes the equalizer valve in fluid passageway 346, thereby isolating the fluid passageway 346 from the annulus 218. In this manner, the equalizer valve in fluid passageway 346 may close before probes 318, 320 may have entered contact with the mud cake that lines the inner wall of wellbore 104. Fluid passageway 346, now closed to annulus 218, is in fluid communication with low volume pump 326.

As low volume pump 326 is actuated, formation fluid may thus be drawn through probe channels 322, 324 and probes 318, 320. The movement of low volume pump 326 lowers the pressure in fluid passageway 346 to a pressure below the formation pressure, such that formation fluid is drawn through probe channels 322, 324 and probes 318, 320 and into fluid passageway 346. Probes 318, 320 serves as a seal to prevent annular fluids from entering fluid passageway 346. Such an operation as described may take place before, after, during or as part of a sampling operation.

With low volume pump 326 in its fully retracted position and formation fluid drawn into fluid passageway 346, the pressure will stabilize and enable pressure sensor 352 to sense and measure formation fluid pressure. The measured pressure is transmitted to information handling system 122 disposed on formation testing tool 100 and/or it may be transmitted to the surface via mud pulse telemetry or by any other conventional telemetry means to an information handling system 122 disposed on surface 112.

During this interval, pressure sensor 352 may continuously monitor the pressure in fluid passageway 346 until the pressure stabilizes, or after a predetermined time interval. When the measured pressure stabilizes, or after a predetermined time interval, for example at 1800 psi, and is sensed by pressure sensor 352 the drawdown operation may be complete.

Next, high-volume bidirectional pump 312 activates and equalizer valve 344 is opened. This allows for formation fluid to move toward high-volume bidirectional pump 312 through passageway 306. Formation fluid moves through passageway 306 to sensor section 332. Once the drilling fluid filtrate has moved into sensor section 332 high-volume bidirectional pump 312 may stop. This may allow the drilling fluid filtrate to be measured by optical measurement tool 334 within sensor section 332. Without limitation, any suitable properties of the formation fluid may be measured. In examples, properties may comprise formation pressure testing performed in a measurement operation.

Formation pressure is the force exerted by fluids contained in pore space of rocks of formation 106. Realtime measurement of this pressure data during drilling operations (i.e., seen in FIG. 2) may enable users to make decisions that may optimize the drilling operation and reduce uncertainties associated with the drilling operation. Formation pressure test results obtained from a wireline operation (i.e., seen in FIG. 1) may allow measuring of formation fluid gradient and fluid mobility. The measurement may be performed using formation testing tool 100 (e.g., referring to FIG. 1) that may be landed a particular depth with wellbore 104 to measure the pressure and mobility of that location. However, the quality of pressure test depends on the chosen location. Landing at a poor location may cause prolonged formation testing time and poor data quality.

Landing formation testing tool 100 (as a wireline or LWD) at a depth with wellbore 104 may improve the quality of formation pressure test (for pressure test) and reduce the pump out time to get clean fluid sample. Landing at a high-quality pressure test location also reduces the testing time as low-quality locations typically take twice as much time to complete with suboptimal testing result. A suboptimal test is one that does not meet the expected quality based on known formation properties. To achieve landing at the high-quality pressure test locations, a correlation log is formed using one or more sensors on formation testing tool 100. A high quality test is one that meets or exceeds the expected quality based on the known formation properties. The correlation log may be a depth log that is formed by measuring depth of formation testing tool 100 in wellbore 104 as it traverses wellbore 104. The correlation log, being formed in real-time is also compared in real-time with an openhole log to estimate the relative shifts between the correlation log and the openhole log. An openhole log is created during drilling operations to map wellbore 104 as it is formed, such as seen in FIG. 2. Additionally, an openhole log may be formed by a wireline tool that traverses the formed wellbore 104 after drilling operations. The relative shifts are applied on the correlation logs to identify the target depth and land formation testing tool 100 at the high-quality pressure test location for a formation pressure test operation. To help ensure that formation testing tool 100 lands on a high-quality pressure test location, a machine learning model may be utilized on one or more information handling systems 122.

Figure 4:
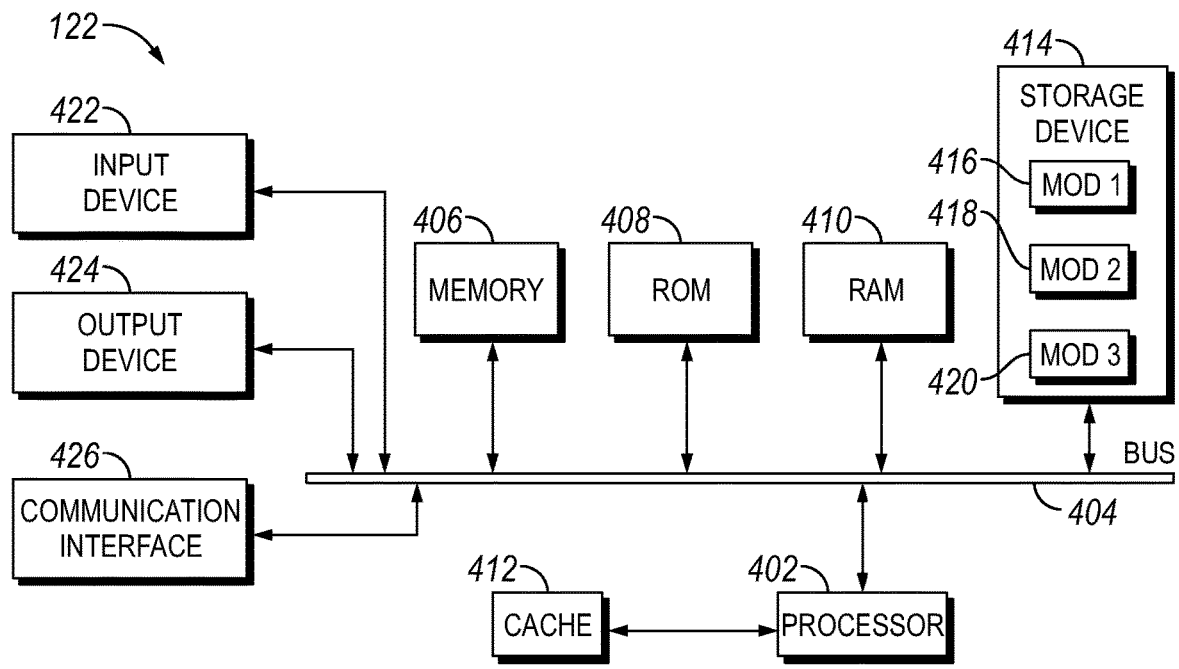
FIG. 4 is a schematic of an information handling system.

FIG. 4 illustrates information handling system 122 which may be employed to perform various blocks, methods, and techniques disclosed herein. As illustrated, information handling system 122 includes a processing unit (CPU or processor) 402 and a system bus 404 that couples various system components including system memory 406 such as read only memory (ROM) 408 and random-access memory (RAM) 410 to processor 402. Processors disclosed herein may all be forms of this processor 402. Information handling system 122 may include a cache 412 of high-speed memory connected directly with, in close proximity to, or integrated as part of processor 402. Information handling system 122 copies data from memory 406 and/or storage device 414 to cache 412 for quick access by processor 402. In this way, cache 412 provides a performance boost that avoids processor 402 delays while waiting for data. These and other modules may control or be configured to control processor 402 to perform various operations or actions. Other system memory 406 may be available for use as well. Memory 406 may include multiple different types of memory with different performance characteristics. It may be appreciated that the disclosure may operate on information handling system 122 with more than one processor 402 or on a group or cluster of computing devices networked together to provide greater processing capability. Processor 402 may include any general-purpose processor and a hardware module or software module, such as first module 416, second module 418, and third module 420 stored in storage device 414, configured to control processor 402 as well as a special-purpose processor where software instructions are incorporated into processor 402. Processor 402 may be a self-contained computing system, containing multiple cores or processors, a bus, memory controller, cache, etc. A multi-core processor may be symmetric or asymmetric. Processor 402 may include multiple processors, such as a system having multiple, physically separate processors in different sockets, or a system having multiple processor cores on a single physical chip. Similarly, processor 402 may include multiple distributed processors located in multiple separate computing devices but working together such as via a communications network. Multiple processors or processor cores may share resources such as memory 406 or cache 412 or may operate using independent resources. Processor 402 may include one or more state machines, an application specific integrated circuit (ASIC), or a programmable gate array (PGA) including a field PGA (FPGA).

Each individual component discussed above may be coupled to system bus 404, which may connect each and every individual component to each other. System bus 404 may be any of several types of bus structures including a memory bus or memory controller, a peripheral bus, and a local bus using any of a variety of bus architectures. A basic input/output (BIOS) stored in ROM 408 or the like, may provide the basic routine that helps to transfer information between elements within information handling system 122, such as during start-up. Information handling system 122 further includes storage devices 414 or computer-readable storage media such as a hard disk drive, a magnetic disk drive, an optical disk drive, tape drive, solid-state drive, RAM drive, removable storage devices, a redundant array of inexpensive disks (RAID), hybrid storage device, or the like. Storage device 414 may include software modules 416, 418, and 420 for controlling processor 402. Information handling system 122 may include other hardware or software modules. Storage device 414 is connected to the system bus 404 by a drive interface. The drives and the associated computer-readable storage devices provide nonvolatile storage of computer-readable instructions, data structures, program modules and other data for information handling system 122. In one aspect, a hardware module that performs a particular function includes the software component stored in a tangible computer-readable storage device in connection with the necessary hardware components, such as processor 402, system bus 404, and so forth, to carry out a particular function. In another aspect, the system may use a processor and computer-readable storage device to store instructions which, when executed by the processor, cause the processor to perform operations, a method or other specific actions. The basic components and appropriate variations may be modified depending on the type of device, such as whether information handling system 122 is a small, handheld computing device, a desktop computer, or a computer server. When processor 402 executes instructions to perform "operations", processor 402 may perform the operations directly and/or facilitate, direct, or cooperate with another device or component to perform the operations.

As illustrated, information handling system 122 employs storage device 414, which may be a hard disk or other types of computer-readable storage devices which may store data that are accessible by a computer, such as magnetic cassettes, flash memory cards, digital versatile disks (DVDs), cartridges, random access memories (RAMs) 410, read only memory (ROM) 408, a cable containing a bit stream and the like, may also be used in the exemplary operating environment. Tangible computer-readable storage media, computer-readable storage devices, or computer-readable memory devices, expressly exclude media such as transitory waves, energy, carrier signals, EM waves, and signals per se.

To enable user interaction with information handling system 122, an input device 422 represents any number of input mechanisms, such as a microphone for speech, a touch-sensitive screen for gesture or graphical input, keyboard, mouse, motion input, speech and so forth. Additionally, input device 422 may receive acoustic or EM measurements from fluid sampling tool 100 (e.g., referring to FIGS. 1 and 2), discussed above. An output device 424 may also be one or more of a number of output mechanisms known to those of skill in the art. In some instances, multimodal systems enable a user to provide multiple types of input to communicate with information handling system 122. Communications interface 426 generally governs and manages the user input and system output. There is no restriction on operating on any particular hardware arrangement and therefore the basic hardware depicted may easily be substituted for improved hardware or firmware arrangements as they are developed.

As illustrated, each individual component describe above is depicted and disclosed as individual functional blocks. The functions these blocks represent may be provided through the use of either shared or dedicated hardware, including, but not limited to, hardware capable of executing software and hardware, such as a processor 402, that is purpose-built to operate as an equivalent to software executing on a general purpose processor. For example, the functions of one or more processors presented in FIG. 5 may be provided by a single shared processor or multiple processors. (Use of the term "processor" should not be construed to refer exclusively to hardware capable of executing software.) Illustrative embodiments may include microprocessor and/or digital signal processor (DSP) hardware, read-only memory (ROM) 408 for storing software performing the operations described below, and random-access memory (RAM) 410 for storing results. Very large-scale integration (VLSI) hardware embodiments, as well as custom VLSI circuitry in combination with a general-purpose DSP circuit, may also be provided.

Figure 5:
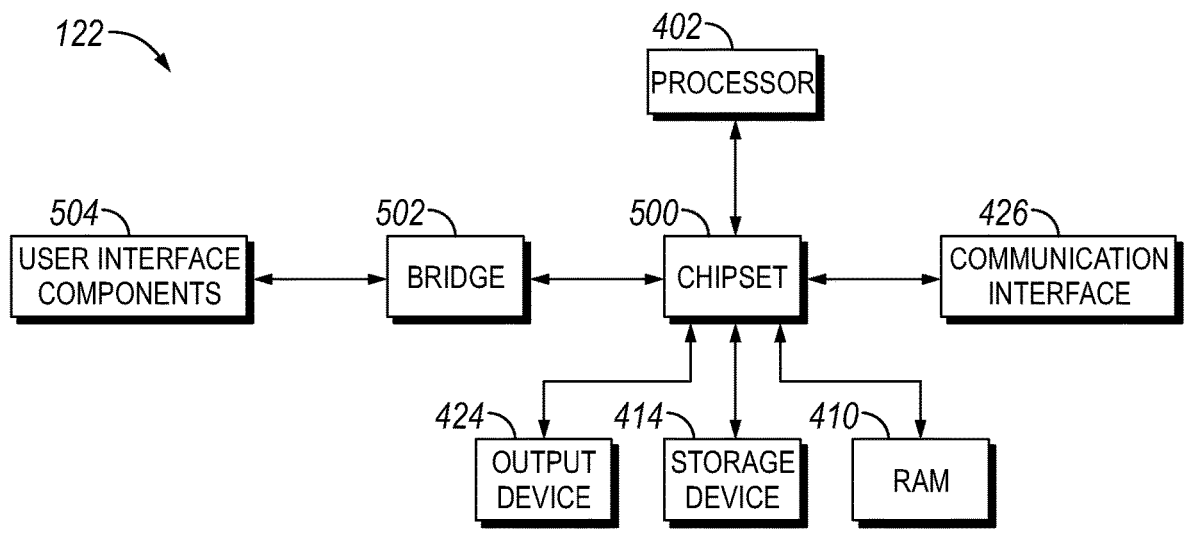
FIG. 5 is a schematic of a chipset that may be utilized by the information handling system.

FIG. 5 illustrates an example information handling system 122 having a chipset architecture for information handling system 122 that may be used in executing the described method and generating and displaying a graphical user interface (GUI). Information handling system 122 is an example of computer hardware, software, and firmware that may be used to implement the disclosed technology. Information handling system 122 may include a processor 402, representative of any number of physically and/or logically distinct resources capable of executing software, firmware, and hardware configured to perform identified computations. Processor 402 may communicate with a chipset 500, discussed below, that may control input to and output from processor 402. In this example, chipset 500 outputs information to output device 424, such as a display, and may read and write information to storage device 414, which may include, for example, magnetic media, and solid-state media. Chipset 500 may also read data from and write data to RAM 410. A bridge 502 for interfacing with a variety of user interface components 504 may be provided for interfacing with chipset 500. Such user interface components 504 may include a keyboard, a microphone, touch detection and processing circuitry, a pointing device, such as a mouse, and so on. In general, inputs to information handling system 122 may come from any of a variety of sources, machine generated and/or human generated.

Chipset 500 may also interface with one or more communication interfaces 426 that may have different physical interfaces. Such communication interfaces may include interfaces for wired and wireless local area networks, for broadband wireless networks, as well as personal area networks. Some applications of the methods for generating, displaying, and using the GUI disclosed herein may include receiving ordered datasets over the physical interface or be generated by the machine itself by processor 402 analyzing data stored in storage device 414 or RAM 410. Further, information handling system 122 receive inputs from a user via user interface components 504 and execute appropriate functions, such as browsing functions by interpreting these inputs using processor 402.

In examples, information handling system 122 may also include tangible and/or non-transitory computer-readable storage devices for carrying or having computer-executable instructions or data structures stored thereon. Such tangible computer-readable storage devices may be any available device that may be accessed by a general purpose or special purpose computer, including the functional design of any special purpose processor as described above. By way of example, and not limitation, such tangible computer-readable devices may include RAM, ROM, EEPROM, CD-ROM or other optical disk storage, magnetic disk storage or other magnetic storage devices, or any other device which may be used to carry or store program code in the form of computer-executable instructions, data structures, or processor chip design. When information or instructions are provided via a network, or another communications connection (either hardwired, wireless, or combination thereof), to a computer, the computer properly views the connection as a computer-readable medium. Thus, any such connection is properly termed a computer-readable medium. Combinations of the above should also be included within the scope of the computer-readable storage devices.

Computer-executable instructions include, for example, instructions and data which cause a general-purpose computer, special purpose computer, or special purpose processing device to perform a certain function or group of functions. Computer-executable instructions also include program modules that are executed by computers in stand-alone or network environments. Generally, program modules include routines, programs, components, data structures, objects, and the functions inherent in the design of special-purpose processors, etc. that perform particular tasks or implement particular abstract data types. Computer-executable instructions, associated data structures, and program modules represent examples of the program code means for executing blocks of the methods disclosed herein. The particular sequence of such executable instructions or associated data structures represents examples of corresponding acts for implementing the functions described in such blocks.

In additional examples, methods may be practiced in network computing environments with many types of computer system configurations, including personal computers, hand-held devices, multi-processor systems, microprocessor-based or programmable consumer electronics, network PCs, minicomputers, mainframe computers, and the like. Examples may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

Figure 6:
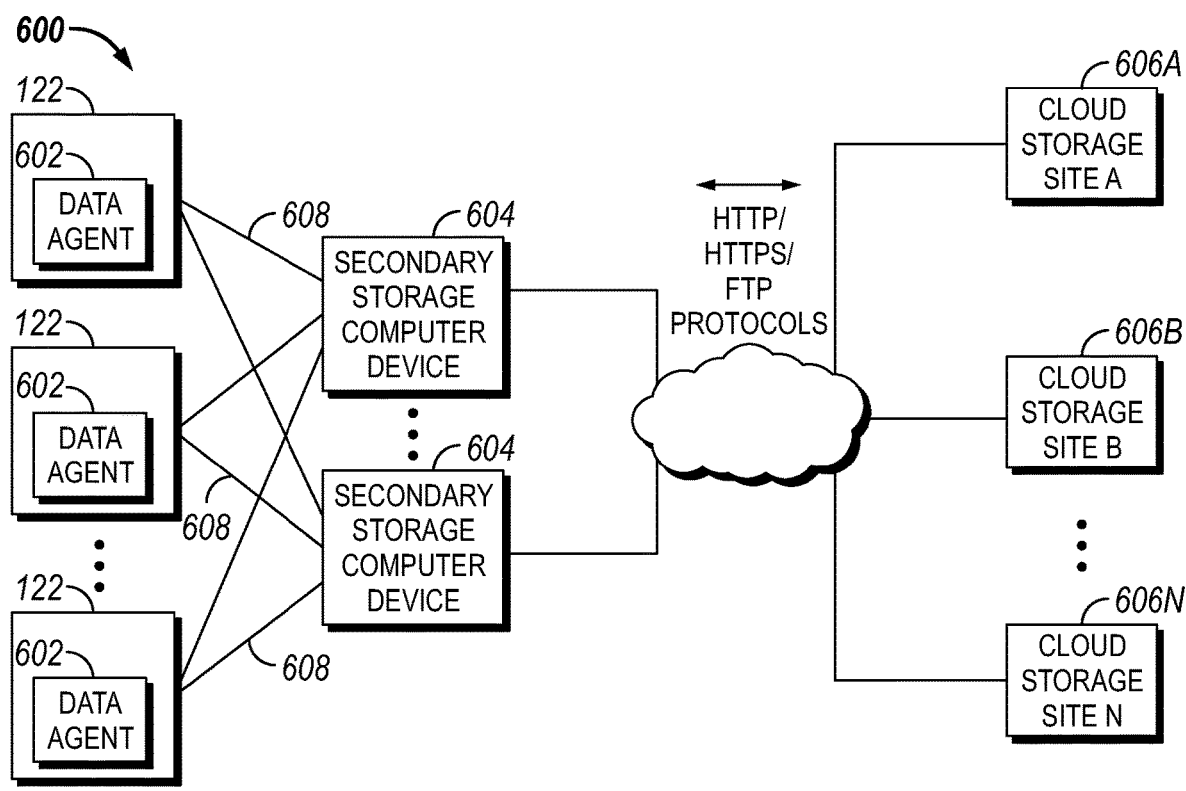
FIG. 6 is a schematic for an arrangement of resources on a computing network.

FIG. 6 illustrates an example of one arrangement of resources on a computing network 600 that may employ the processes and techniques described herein, although many others are of course possible. As noted above, an information handling system 122, as part of their function, may utilize data, which includes files, databases, directories, metadata (e.g., access control list (ACLS) creation/edit dates associated with the data, etc.), and other data objects. The data on the information handling system 122 is typically a primary copy (e.g., a production copy). During a copy, backup, archive or other storage operation, information handling system 122 may send a copy of some data objects (or some components thereof) to a secondary storage computing device 604 by utilizing one or more data agents 602.

A data agent 602 may be a desktop application, website application, or any software-based application that is run on information handling system 122. As illustrated, information handling system 122 may be disposed at any rig site (e.g., referring to FIG. 1), off site location, core laboratory, repair and manufacturing center, and/or the like. In examples, data agent 602 may communicate with a secondary storage computing device 604 using communication protocol 608 in a wired or wireless system. Communication protocol 608 may function and operate as an input to a website application. In the website application, field data related to pre- and post-operations, generated DTCs, notes, and/or the like may be uploaded. Additionally, information handling system 122 may utilize communication protocol 608 to access processed measurements, operations with similar DTCs, troubleshooting findings, historical run data, and/or the like. This information is accessed from secondary storage computing device 604 by data agent 602, which is loaded on information handling system 122.

Secondary storage computing device 604 may operate and function to create secondary copies of primary data objects (or some components thereof) in various cloud storage sites 606A-N. Additionally, secondary storage computing device 604 may run determinative algorithms on data uploaded from one or more information handling systems 122, discussed further below. Communications between the secondary storage computing devices 604 and cloud storage sites 606A-N may utilize REST protocols (Representational state transfer interfaces) that satisfy basic C/R/U/D semantics (Create/Read/Update/Delete semantics), or other hypertext transfer protocol ("HTTP")-based or file-transfer protocol ("FTP")-based protocols (e.g., Simple Object Access Protocol).

In conjunction with creating secondary copies in cloud storage sites 606A-N, the secondary storage computing device 604 may also perform local content indexing and/or local object-level, sub-object-level or block-level deduplication when performing storage operations involving various cloud storage sites 606A-N. Cloud storage sites 606A-N may further record and maintain, EM logs, map DTC codes, store repair and maintenance data, store operational data, and/or provide outputs from determinative algorithms that are located in cloud storage sites 606A-N. In a non-limiting example, this type of network may be utilized as a platform to store, backup, analyze, import, preform extract, transform and load ("ETL") processes, mathematically process, apply machine learning models, and augment data sets.

A machine learning model may be an empirically derived model which may result from a machine learning algorithm identifying one or more underlying relationships within a dataset. In comparison to a physics-based model, such as Maxwell's Equations, which are derived from first principals and define the mathematical relationship of a system, a pure machine learning model may not be derived from first principals. Once a machine learning model is developed, it may be queried in order to predict one or more outcomes for a given set of inputs. The type of input data used to query the model to create the prediction may correlate both in category and type to the dataset from which the model was developed.

The structure of, and the data contained within a dataset provided to a machine learning algorithm may vary depending on the intended function of the resulting machine learning model. The rows of data, or data points, within a dataset may contain one or more independent values. Additionally, datasets may contain corresponding dependent values. The independent values of a dataset may be referred to as "features," and a collection of features may be referred to as a "feature space." If dependent values are available in a dataset, they may be referred to as outcomes or "target values." Although dependent values may be a necessary component of a dataset for certain algorithms, not all algorithms may utilize a dataset with dependent values. Furthermore, both the independent and dependent values of the dataset may comprise either numerical or categorical values.

While it may be true that machine learning model development is more successful with a larger dataset, it may also be the case that the whole dataset isn't used to train the model. A test dataset may be a portion of the original dataset which is not presented to the algorithm for model training purposes. Instead, the test dataset may be used for what may be known as "model validation," which may be a mathematical evaluation of how successfully a machine learning algorithm has learned and incorporated the underlying relationships within the original dataset into a machine learning model. This may include evaluating model performance according to whether the model is over-fit or under-fit. As it may be assumed that all datasets contain some level of error, an evaluation and/or optimization of the model performance and associated model fit by means of model validation may be performed. In general, the variability in model fit (e.g.: whether a model is over-fit or under-fit) may be described by the "bias-variance trade-off." As an example, a model with high bias may be an under-fit model, where the developed model is over-simplified, and has either not fully learned the relationships within the dataset or has over-generalized the underlying relationships. A model with high variance may be an over-fit model which has overlearned about non-generalizable relationships within training dataset which may not be present in the test dataset. In a non-limiting example, these non-generalizable relationships may be driven by factors such as intrinsic error, data heterogeneity, and the presence of outliers within the dataset. The selected ratio of training data to test data may vary based on multiple factors, including, in a non-limiting example, the homogeneity of the dataset, the size of the dataset, the type of algorithm used, and the objective of the model. The ratio of training data to test data may also be determined by the validation method used, wherein some non-limiting examples of validation methods include k-fold cross-validation, stratified k-fold cross-validation, bootstrapping, leave-one-out cross-validation, resubstituting, random sub-sampling, and percentage hold-out.

In addition to the parameters that exist within the dataset, such as the independent and dependent variables, machine learning algorithms may also utilize parameters referred to as "hyperparameters." Each algorithm may have an intrinsic set of hyperparameters which guide what and how an algorithm learns about the training dataset by providing limitations or operational boundaries to the underlying mathematical workflows on which the algorithm functions. Furthermore, hyperparameters may be classified as either model hyperparameters or algorithm parameters.

Model hyperparameters may guide the level of nuance with which an algorithm learns about a training dataset, and as such model hyperparameters may also impact the performance or accuracy of the model that is ultimately generated. Modifying or tuning the model hyperparameters of an algorithm may result in the generation of substantially different models for a given training dataset. In some cases, the model hyperparameters selected for the algorithm may result in the development of an over-fit or under-fit model. As such, the level to which an algorithm may learn the underlying relationships within a dataset, including the intrinsic error, may be controlled to an extent by tuning the model hyperparameters.

Model hyperparameter selection may be optimized by identifying a set of hyperparameters which minimize a predefined loss function. An example of a loss function for a supervised regression algorithm may include the model error, wherein the optimal set of hyperparameters correlates to a model which produces the lowest difference between the predictions developed by the produced model and the dependent values in the dataset. In addition to model hyperparameters, algorithm hyperparameters may also control the learning process of an algorithm, however algorithm hyperparameters may not influence the model performance. Algorithm hyperparameters may be used to control the speed and quality of the machine learning process. As such, algorithm hyperparameters may affect the computational intensity associated with developing a model from a specific dataset.

Machine learning algorithms, which may be capable of capturing the underlying relationships within a dataset, may be broken into different categories. One such category may include whether the machine learning algorithm functions using supervised, unsupervised, semi-supervised, or reinforcement learning. The objective of a supervised learning algorithm may be to determine one or more dependent variables based on their relationship to one or more independent variables. Supervised learning algorithms are named as such because the dataset includes both independent and corresponding dependent values where the dependent value may be thought of as "the answer," that the model is seeking to predict from the underlying relationships in the dataset. As such, the objective of a model developed from a supervised learning algorithm may be to predict the outcome of one or more scenarios which do not yet have a known outcome. Supervised learning algorithms may be further divided according to their function as classification and regression algorithms. When the dependent variable is a label or a categorical value, the algorithm may be referred to as a classification algorithm. When the dependent variable is a continuous numerical value, the algorithm may be a regression algorithm. In a non-limiting example, algorithms utilized for supervised learning may include Neural Networks, K-Nearest Neighbors, Naïve Bayes, Decision Trees, Classification Trees, Regression Trees, Random Forests, Linear Regression, Support Vector Machines (SVM), Gradient Boosting Regression, and Perception Back-Propagation.

The objective of unsupervised machine learning may be to identify similarities and/or differences between the data points within the dataset which may allow the dataset to be divided into groups or clusters without the benefit of knowing which group or cluster the data may belong to. Datasets utilized in unsupervised learning may not include a dependent variable as the intended function of this type of algorithm is to identify one or more groupings or clusters within a dataset. In a non-limiting example, algorithms which may be utilized for unsupervised machine learning may include K-means clustering, K-means classification, Fuzzy C-Means, Gaussian Mixture, Hidden Markov Model, Neural Networks, and Hierarchical algorithms.

Figure 7:
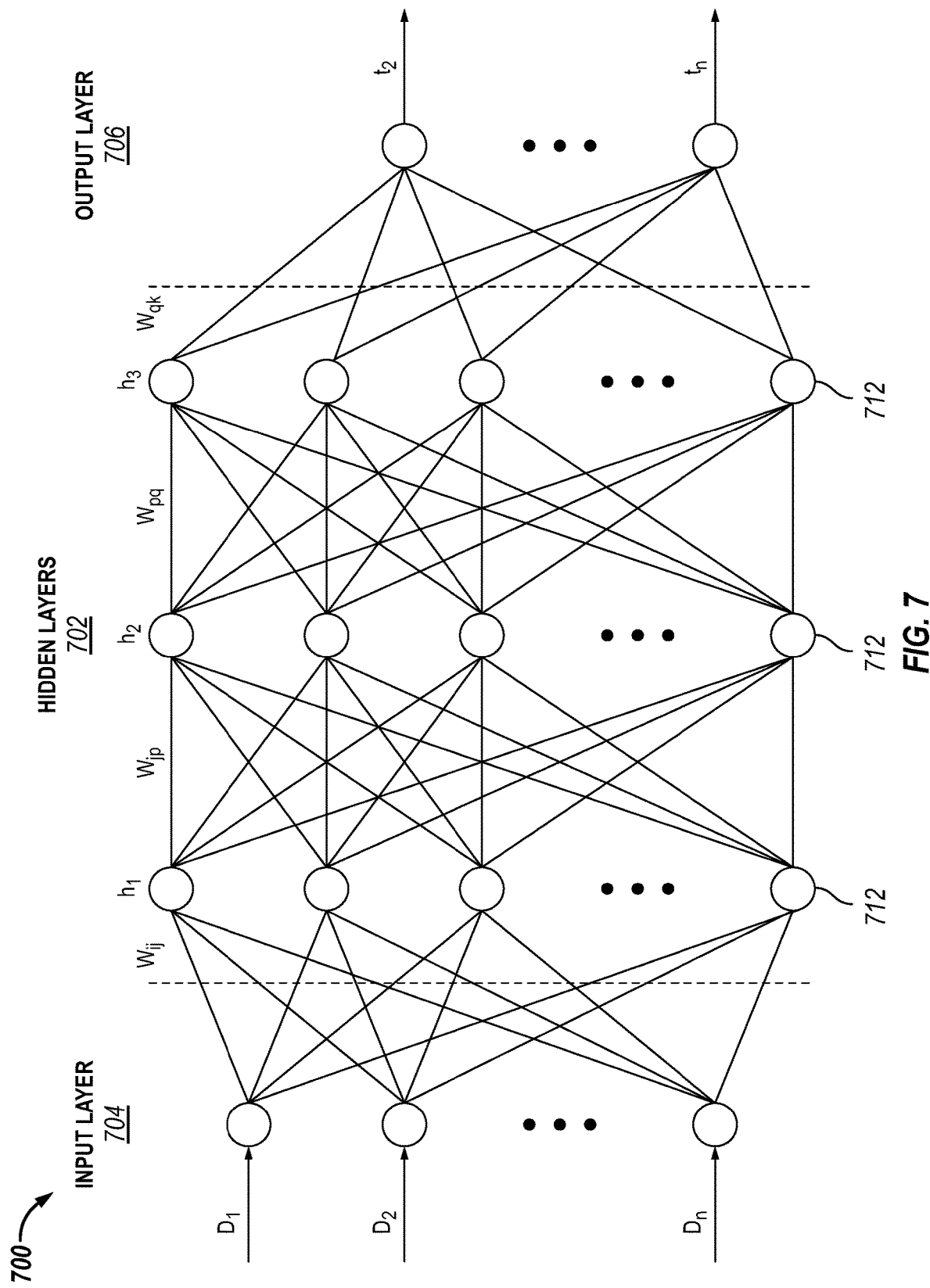
FIG. 7 is a schematic for a neural network.

In examples to determine a relationship using machine learning, a neural network (NN) 700, as illustrated in FIG. 7, may be utilized. A NN 700 is an artificial neural network with one or more hidden layers 702 between input layer 704 and output layer 706. During operations, input data is taken by neurons 712 in first layer which then provides an output to the neurons 712 within next layer and so on which provides a final output in output layer 706. Each layer may have one or more neurons 712. The connection between two neurons 712 of successive layers may have an associated weight. The weight defines the influence of the input to the output for the next neuron 712 and eventually for the overall final output.

For a formation pressure test operation, based on a large historical database, which include both openhole logs and formation testing quality result, a machine learning method may be applied to develop multivariate correlation between openhole logs and a formation pressure test quality index. In examples, openhole lots may be formed from one or more sensors that take one or more gamma ray measurements, one or more resistivity measurements, one or more density measurements, one or more neutron measurements, one or more borehole images, and/or the like. Without limitations, openhole logs may also comprise resistivity measurements, porosity measurements, density measurements, photoelectric (PE) measurements, caliper measurements, acoustic porosity measurements, nuclear magnetic resonance (NMR) measurements, gamma ray spectroscopy measurements, and/or the like. The machine learning model may be validated with a cross-validation and/or a blind test. With this predictive model, a user may use openhole logs as inputs to predict the pressure tests' quality index for one or more locations in wellbore 104 and identify locations that meet the test program's objective. The machine learning model may be a classification model or a regression model. In examples, the machine learning model may be performed on one or more information handling systems 122, using the methods and systems described above. For formation pressure test location selection, one may use numerical or proxy formation test simulation model to predict pressure testing operational time based on an openhole log, reservoir zone properties and sampling tool/pad parameters. Locations with the shortest operational time to perform a pressure test may be recommended for each zone.

Figure 8:
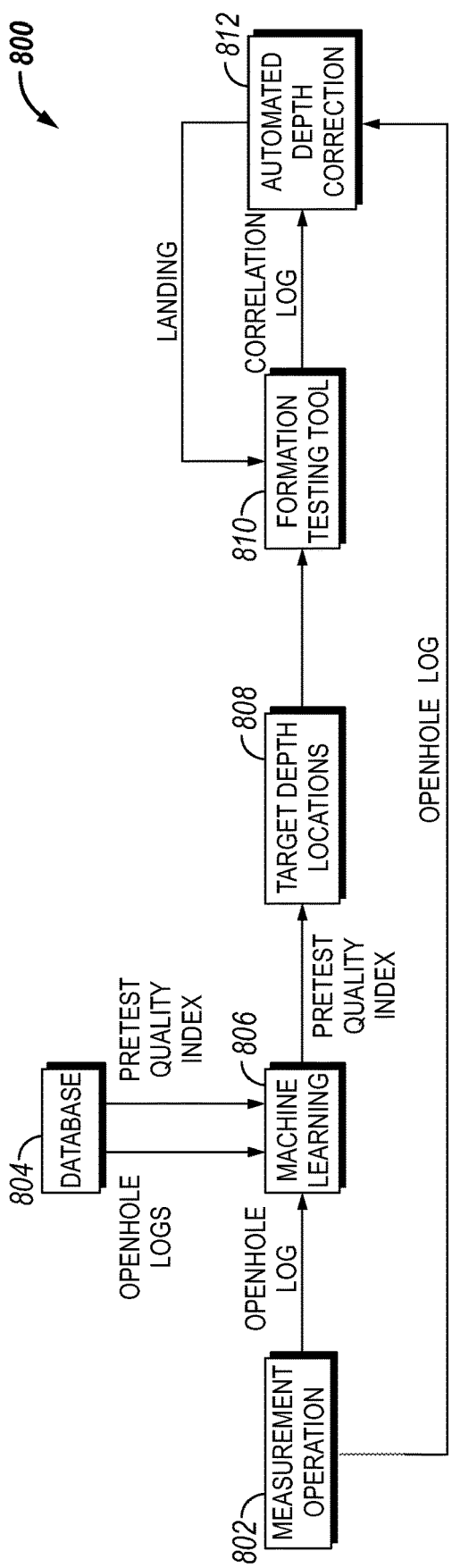
FIG. 8 is a workflow for capturing pressure data using the formation sampling tool.

FIG. 8 illustrates workflow 800 for capturing pressure data using formation sampling tool 100 (e.g., referring to FIGS. 1 and 2) during a pressure testing operation. Workflow 800 may begin with block 802 in which a measurement operation to form an openhole log is performed using a wireline based system (i.e., FIG. 1) or a logging while drilling system (i.e., FIG. 2). In block 804, a database, which may be a set of data inclusive of data with at least one common relation, for example, measured depth or time, is formed and/or populated with openhole logs and corresponding pretext quality index at least one wellbore 104 but may comprise several well sites. The database may be formed, operate, and/or function according to methods and systems discussed above utilizing a computing network 600 (e.g., referring to FIG. 6) and NN 700 (e.g., referring to FIG. 7). The logs and quality indexes may come from previous operations in wellbore 104 or neighboring wellbores (not illustrated). The database in block 804 may be utilized to train a machine learning model in block 806. The trained machine learning model in block 806 may then be utilized to create a pretext quality index for the current measurement operation. The quality of a pressure test is measured based on desirable characteristics of the pressure change with respect to time such as but not limited to buildup time, buildup stability, asymptote stability, drawdown stability, wherein stability is judged based on a relative change in a parameter, or smoothness of the transient. Such scoring may be qualitative or quantitative. Multiple scoring criteria may be combined to form a composite quality index.

A pretext quality index may comprise one or more predictions for one or more locations within wellbore 104 as to the quality of pressure measurements that may be taken at the one or more locations. Based on the predicted pretext quality index, target depth locations for obtaining high quality pressure measurements may be identified by predicted high quality index locations in block 808 using the trained machine learning model. For example, the trained machine learning model may predict the quality of pressure testing at one or more locations within wellbore 104 and create a corresponding index that is associated for the one or more locations. The locations with a high index, from the predicted pretext quality index (i.e., above a predefined threshold), are chosen locations to perform a pressure test. In block 810, formation sampling tool 100 may then be moved toward locations in wellbore 104 identified in block 808. As formation sampling tool 100 moves through wellbore 104, a correlation log may be created by formation sampling tool 100, as described above. The correlation log may be a depth log that is formed by measuring depth of formation testing tool 100 in wellbore 104 as it traverses wellbore 104. In block 812 a depth-matching between the correlation log and the openhole log is performed. For example, the locations from block 808 and/or the depths in the openhole log from block 802 may be matched (i.e., mapped) to the correlation log created in block 810 with real-time automated depth shift corrections, using a relative shift table, to land formation sampling tool 100 at a chosen location within wellbore 104. Automated depth correction between the openhole log and the correlation log to create the relative shift table may be performed using one of two algorithms, namely, window-based (WB) alignment and edge-based (EB) alignment.

Figure 9:
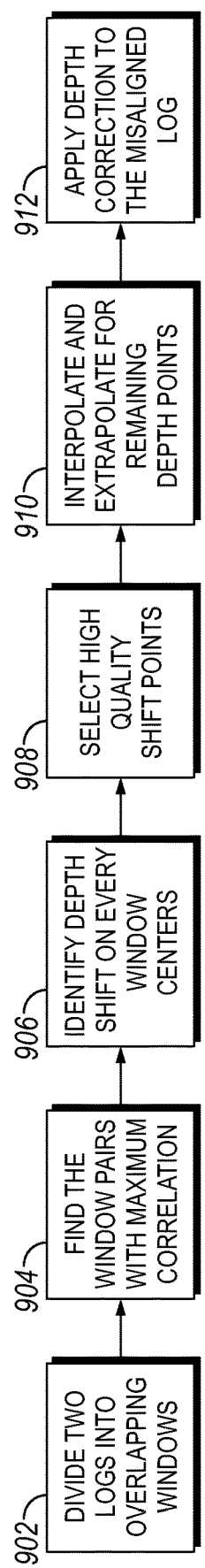
FIG. 9 is a workflow for aligning an openhole log and a correlation log using window-based (WB) correlation.

FIG. 9 illustrates workflow 900 for aligning an openhole log and a correlation log using window-based correlation. Workflow 900 may begin with block 902 in which both logs may be divided using one or more windows that may overlap. In block 904, the correlation data between every pair of windowed logs may be computed to find one or more pairs of windows that correlate greater than any other pair of windows in the correlation data. In block 906, the distance between the center of the windows with highest correlation gives the shift that needs to be applied at the window centers to align the two logs. During operations, there may be a plurality of shifts identified that may be used to populate a relative shift table. A relative shift is a section of depth in a log that is moved as a block in order to align the responses of sensors form a separate pass. It should be noted that shift computations are independent of speed calculations. The shifts only consider the relative change in depth for the significant features between an openhole log and a correlation log. The relative shift table populates the shift in the location of the center of windows between openhole log and the correlation log. In block 908, the shift data at the center of all the windows may be updated using an optimization algorithm or median filter to ensure monotonicity between a depth aligned log a misaligned log and to ensure that significant features are aligned properly. Optimization algorithms may be linear or nonlinear and comprise gradient decent methods, moment methods, Hessian methods, evolutionary methods, grid search methods, and/or simplex methods. In block 910, for additional depth points outside of the windows created and altered in blocks 902 through 908, the shift values may be computed using interpolation and extrapolation and may be conducted as an example with linear methods, spline methods, and/or machine learning methods. Using the information in blocks 908 and 910, a depth correction may be applied to the misaligned log in block 912. Additionally, a quality control indicator may be utilized to ensure only high quality shifts or mapping points are applied to achieve the depth alignment. Such quality control features may be the correlation coefficient or squared correlation coefficient standard error estimate between the characteristics of the significant features. In other examples, an edge-based correlation may be utilized in place of a window-based correlation with or without a quality indicator.

Figure 10:
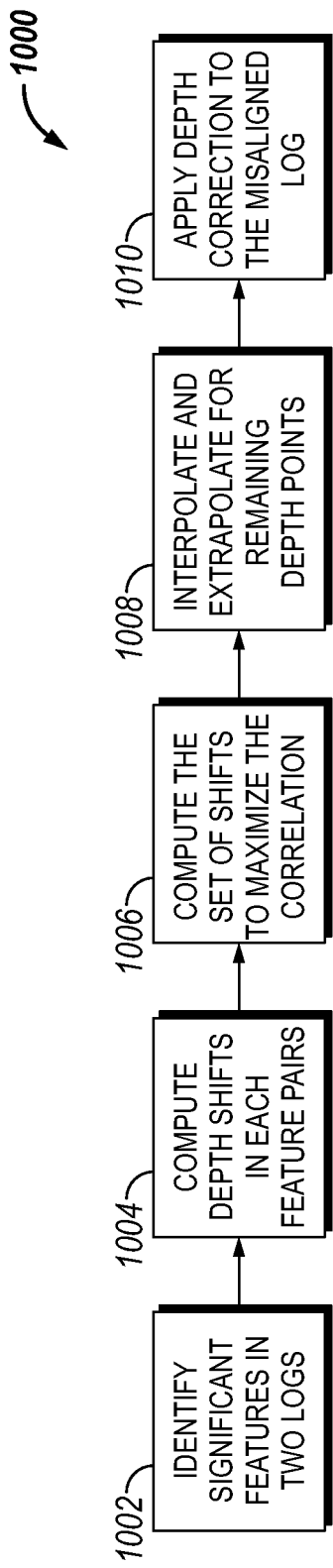
FIG. 10 is a workflow for aligning two logs using an edge-based (EB) correlation.

FIG. 10 illustrates workflow 1000 for aligning two logs using an edge-based correlation. Workflow 1000 may begin with block 1002 in which significant features, which may be identified as a high likelihood of occurring in both a reference log and a log being aligned, in an openhole log and a correlation log may be identified. Significant features are defined as high energy patterns in the logs that are distinguishable from a low energy background. Users may identify the significant features from a visual plot of the signal. In block 1004, a table of all possible shifts, within a shift tolerance defined by the desired resolution of alignment such as two feet (six meters), one foot (three meters), six inches (fifteen cm), three inches (eight cm), 2 inches (five cm), or less than two inches (five cm), that may produce the given significant feature shifts in the two logs are listed. In some relatively homogenous formations, lower resolution may be sufficient, or in highly changing formations such as those with thinly laminated beds, high resolution may be desired. Subsequently, in block 1006, in examples a number of resultant shifts may be tried and the set of shifts that give the highest correlation is selected. In block 1008, using interpolation and extrapolation, the depth shifts at the remaining depth points are computed. During operations, there may be a plurality of shifts identified that may be used to populate a relative shift table. The relative shift table shows the amount a log would have to be shifted within a narrow depth window as a function of the depth specification of that depth window which may include a mean depth of the window or starting depth of the window or end depth of the window or the like. The depth table may either relate the table to be aligned to the reference, but in some embodiments may align the reference to working log. In the case of feature-based alignment, discussed below that identifies significant features, the depth reference may be the position of the feature but may also be an asymmetric position between features. Additionally, a relative shift table comprises the shift values at selected depth points that may be applied on a misaligned log to obtain the alignment. For depth points not listed in the relative shift table, interpolation and extrapolation may be used to obtain the shift in depths. In examples, a relative shift table may comprise the shift values at selected depths. A dynamically calibrated depth panel uses the computed shift table to correct the depth displayed on the panel in real-time so that a user may land formation sampling tool 100 at a depth selected using the methods above when that value shows on the panel.

Using the information from block 1006 and 1008, a depth shift is applied on the misaligned log to obtain the log with alignment in block 1010. Both an edge-based correlation and a window-based correlation may be utilized individually or together for correcting the misaligned log. In other examples, dynamic time warping (DTW) may be utilized as an alternative to or complement to window-based correlation and/or edge-based correlation. DTW is an optimization algorithm that uses minimization of a misfit between two logs to perform the alignment. The misfit function is a 'distance' measurement between the two logs. The minimum misfit is expected to align the two logs.

Figure 11:
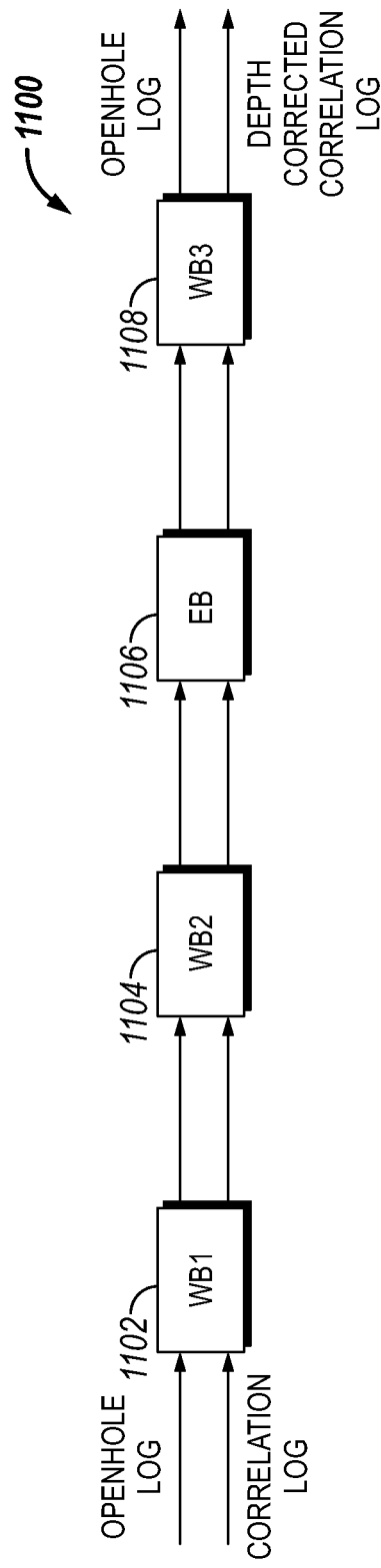
FIG. 11 is a workflow for correcting a correlation log.

FIG. 11 illustrates workflow 1100 for correcting a correlation log using methods discussed above in FIGS. 9 and 10. Multiple iterations of window or edge based (also referred to as feature-based alignment) correlation or combinations therein may be performed. Window based correlation may be easier to perform and larger windows may provide a coarse alignment. A feature-based alignment may benefit from a window-based alignment in that correlative features may be identified with higher confidence. The feature-based alignment has the potential for a very high accuracy, but may lack precision if features are sparse. A narrower window based alignment may benefit from a subsequent feature-based alignment. Feature and window based alignments may be performed iteratively and intermingled to optimally align a set of logs. As noted above, the correlation log is the log formed by a formation sampling tool 100 (e.g., referring to FIG. 1) during downhole operations. Workflow 1100 may begin with block 1102 in which an openhole log and a correlation log may be fed into a first window-based (WB) alignment algorithm. The outputs from block 1102 may be fed to the second WB aligner in block 1104, which performs a finer correlation alignment, whose outputs are fed to an edge-based (EB) aligner in block 1106. Its outputs from block 1106 are fed to the final WB aligner in block 1108 which works on very fine windows to obtain a final depth correction on the correlation log. It should be noted that workflow 1100 is not specific to the order discussed above. Workflow 1100 may have any arrangement of WB and EB algorithms as well as any number of WB and EB algorithms in workflow 1100. Additionally, each WB and EB may have different properties. Multiple corrections, using WB and/or EB algorithms, may be used to align different classes of significant features. For some significant features, it is easier to compute the shift based on the overall shape of the significant feature. In other examples, the edges of the significant feature are prominent, that may be used to obtain the shift values. Table 1 below illustrates different properties that may be chosen for each WB and EB correction. Correlation may be performed on the raw sensors values of the log, an order derivative with respect to depth (or depth equivalent dimension) or may be performed on other transformed feature space for instance logarithm transformed or combined log space. For example, window sizes, the maximum allowed shifts in each of the alignment steps involved, and/or the like.

TABLE 1

|  | WB1 | WB2 | EB | WB3 |
|---|---|---|---|---|
| Window Size (ft) | 50 | 15 | 50 | 4 |
| Max Shift (ft) | 15 | 4 | N/A | 2 |
| Shift Step (ft) | 1 | 0.5 | N/A | 0.25 |

Figures 12A, 12B:
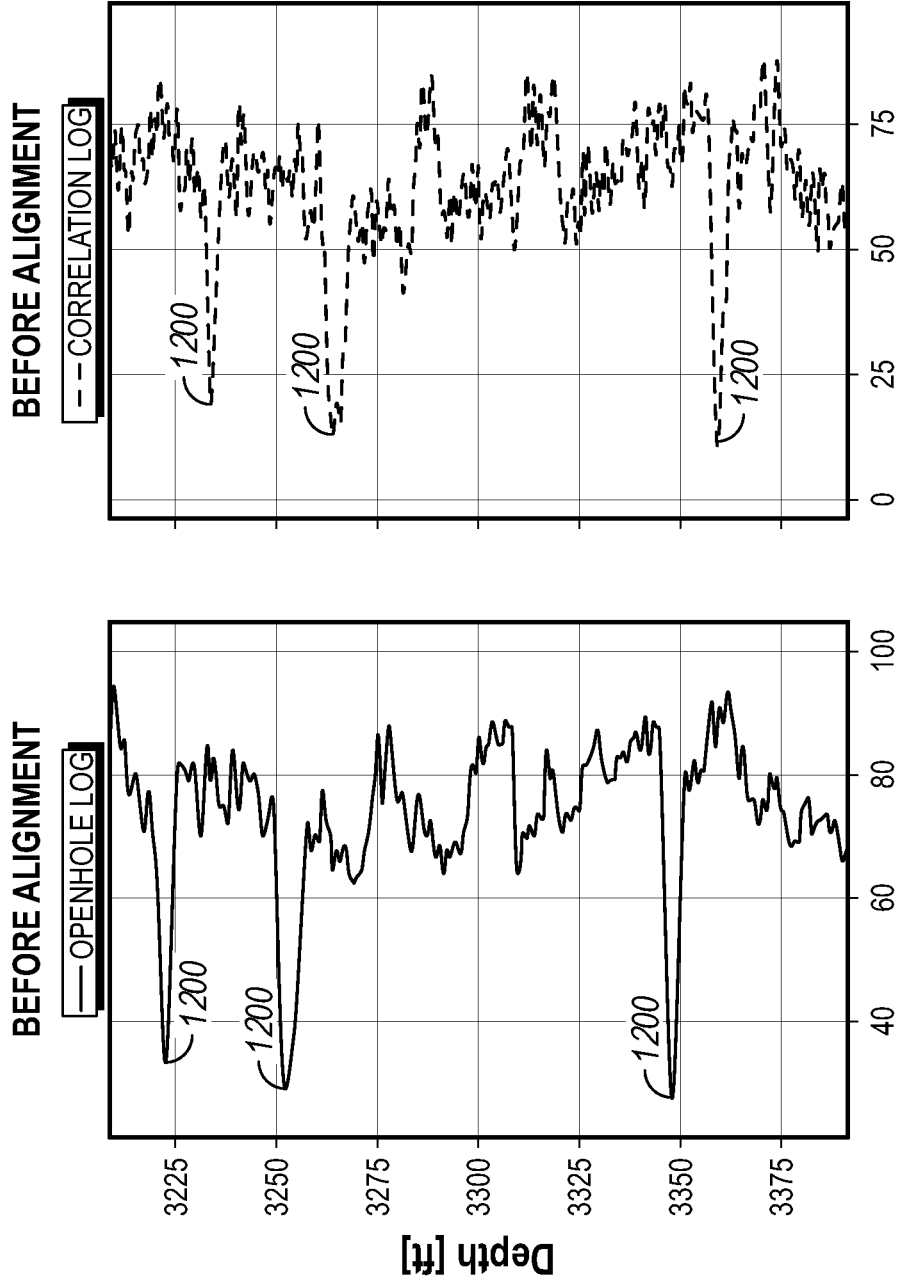
FIGS. 12A-12D are graphs display the results of automated depth correction applied on a given correlation log based on an openhole log.
Figure 12D:
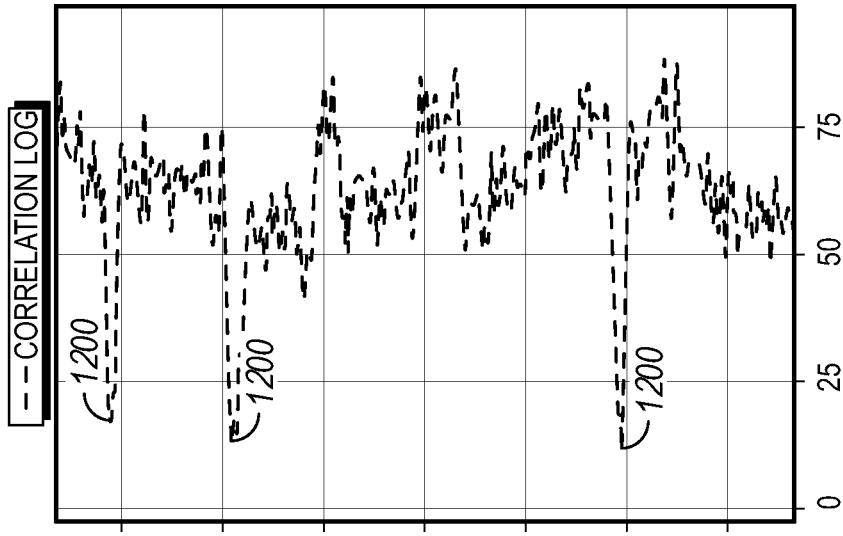
Figure 12C:
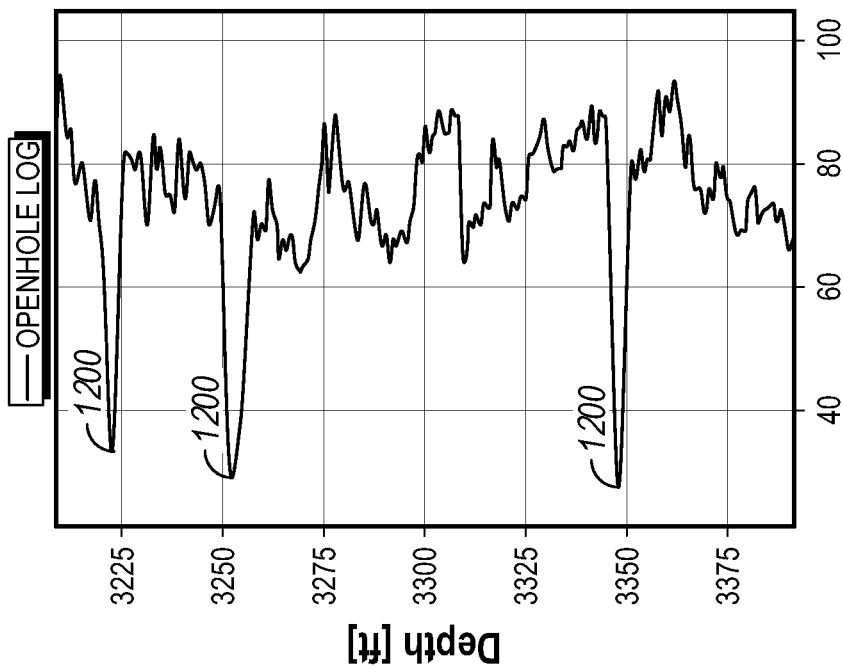

FIGS. 12A-12D display the results of a depth correction that may be applied on a given correlation log based on an openhole log. FIGS. 12A & 12B illustrate graphs that illustrate both the logs for a given depth range before performing alignment. The graphs show significant features 1200, where the log values are much lower than the rest of the depths, are displayed at different depths in both logs. Using openhole log as the reference and workflows 800-1100, a correlation log is depth aligned to shift the location of significant features to the same depth. FIGS. 12C & 12D illustrate graphs that illustrate two logs after performing alignment. As illustrated in FIGS. 12C & 12D, the significant features 1200 are displayed at the same depths in both logs. After openhole logs are used to identify target testing points, those with high likelihood of pretest quality, correlation log from the formation testing pass is depth corrected in real-time to accurately map the testing points onto the correlation logs. A user may land formation sampling tool 100 (e.g., referring to FIGS. 1 and 2) on the depth-corrected target testing points based on the aligned correlation logs. The methods and systems discussed above may also be utilized for other operations outside of landing a formation sampling tool 100 at a specified depth within wellbore 104 (e.g., referring to FIGS. 1 and 2).

As noted above, a correlation log may be utilized with regard to formation sampling tool 100 being lowered into wellbore 104 in order to land formation sampling tool 100 at a location of interest. This location of interest may be a location of desired pressure testing, desired sampling, or other desired stationary operation. As formation sampling tool 100 reaches the location of interest, it may be desirable to pass the location of interest by a distance and align on a slow pass on the up direction. In some embodiments, it may be desirable to pass all desired stationary operational locations and move up to perform operations at each location of interest. In some embodiments, it may be desirable to conduct multiple passes in order to ensure features or windows may be well characterized, and to iteratively home in on the location of interest. Automated software may perform these procedures, and or alert a user for intervention should the desired log correlation be difficult. Additionally, a location of interest may be unidirectionally approached in some embodiments. In other embodiments, a double sensor located on the formation sampling tool 100 (i.e., natural gamma sensor), may be located above and below a landing device (i.e., a formation probe including but not limited to a pad or a packer) disposed on formation sampling tool 100. The double sensor may be used to pre-emptively locate the alignment position of the alternate sensor to provide the landing based on features or correlative windows of formation 104.

The methods and systems described above may be utilized for coring operations. The success of rock characterization study based on coring depends on the quality of the core material that is collected. An efficient coring operation may provide maximum recovery with minimum damage to the rock. Coring operations may rely on identification of depth points that represent the formation inside wellbore 104 (e.g., referring to FIG. 1) and collection core data precisely from these depths. The automated depth correction used for landing the formation testing tool may be extended to coring technology to perform cost effective and quality coring. Other types of operations may also be utilized these methods and systems.

Perforation and fracking operations may also rely on identifying locations within wellbore 104 (e.g., referring to FIG. 1) precisely. The production success of an oil well may depend on the quality of perforation. To perforate at the chosen locations, operators may need to estimate the critical locations ideal for perforation. To successfully perforate at the ideal locations, automated depth correction may be utilized to account for the depth shifts incorporated before perforation. The same workflow may be applied to fracking to land the fracking tools at target depth points delineated from previous open-hole logs.

Improvements over the current art are found in the high-quality pretest results that are obtained using machine learning techniques applied to large database containing openhole logs and corresponding pretest quality index. High quality pressure test locations are identified based on the pretest results generated while drilling. A formation tester may then be landed on the high-quality pressure test location using an automated shift correction applied in real-time on the correlation log based on the openhole logs. Additionally, an ability to accurately target a position based on the characteristics derived in a reference log is not disclosed in current technology, thus, formation testing operations may be better performed. In general, any operation which has stationary requirements and exact location requirements may benefit from this procedure. Well testing or drill stem testing, stimulation, well remediations may be such operations. The ability to target specific locations may reduce expenses of the operation, reduce time for success of operations, and provide for higher success of operations Statement 1: A method may comprise reviewing an openhole log to identify one or more depths within a wellbore for testing, disposing a fluid sampling tool into the wellbore, and creating a correlation log with the fluid sampling tool. The method may further comprise depth-matching the correlation log to the openhole log to create a relative shift table and moving the fluid sampling tool to the one or more depths within the wellbore based at least in part on the relative shift table.

Statement 2: The method of statement 1, wherein the depth-matching is performed with a window-based correlation, an edge-based matching, or a dynamic time warping.

Statement 3: The method of statement 2, wherein the window-based correlation, the edge-based matching, or the dynamic time warping are used in a machine learning model to estimate one or more relative shifts that populate the relative shift table.

Statement 4: The method of statement 2, wherein the window-based correlation further comprises overlapping the correlation log and the openhole log, computing a correlation between the correlation log and the openhole log, identifying a depth shift to correlate between the correlation log and the openhole log, interpolating and extrapolating additional depth points based at least in part on the depth shift, and applying a depth correction to the correlation log.

Statement 5: The method of statement 2, wherein the edge-based matching further comprises identifying one or more significant features in the correlation log and the openhole log, computing one or more depth shifts based at least in part on the one or more significant features between the correlation log and the openhole log, computing a correlation between the correlation log and the openhole log using the one or more depth shifts, interpolating and extrapolating additional depth points based at least in part on the correlation, and applying a depth correction to the correlation log.

Statement 6: The method of any previous statements 1 or 2, the openhole log is formed from one or more gamma ray measurements, one or more resistivity measurements, one or more density measurements, one or more neutron measurements, or one or more borehole images.

Statement 7: The method of any previous statements 1, 2, or 6, wherein the correlation log is formed in real-time.

Statement 8: The method of statement 7, wherein the depth-matching is performed in real-time based at least in part on the correlation log.

Statement 9: The method of any previous statements 1, 2, 6, or 7, further comprising generating the correlation with a gamma ray sensor.

Statement 10: The method of any previous statements 1, 2, 6, 7, or 9, further comprises aligning one or more significant features on the correlation log to the one or more significant features on the openhole log during the depth-matching.

Statement 11: The method of any previous statements 1, 2, 6, 7, 9, or 10, further comprising forming a dynamically calibrated depth panel from the relative shift table.

Statement 12: The method of statement 11, further comprising landing the fluid sampling tool at the one or more depths when a difference between the dynamically calibrated depth panel and the one or more depths is below a threshold.

Statement 13: A system may comprise a fluid sampling tool disposed in a wellbore to create a correlation log and an information handling system connected to the fluid sampling tool. The information handling system may be configured to identify one or more depths within the wellbore for testing using an openhole log, create the correlation log with the fluid sampling tool, depth-match the correlation log to the openhole log to create a relative shift table, and instruct the fluid sampling tool to move to the one or more depths within the wellbore based at least in part on the relative shift table.

Statement 14: The system of statement 13, wherein the depth-match is performed with a window-based correlation, an edge-based matching, or a dynamic time warping.

Statement 15: The system of statement 14, wherein the window-based correlation, the edge-based matching, or the dynamic time warping are used in a machine learning model to estimate one or more relative shifts that populate the relative shift table.

Statement 16: The system of statement 14, wherein the information handling system further utilizes the window-based correlation to overlap the correlation log and the openhole log, compute a correlation between the correlation log and the openhole log, identify a depth shift to correlate between the correlation log and the openhole log, interpolate and extrapolating additional depth points based at least in part on the depth shift, and apply a depth correction to the correlation log.

Statement 17: The system of statement 14, wherein the information handling system further utilizes the edge-based matching to identify one or more significant features in the correlation log and the openhole log, compute one or more depth shifts based at least in part on the one or more significant features between the correlation log and the openhole log, compute a correlation between the correlation log and the openhole log using the one or more depth shifts, interpolate and extrapolating additional depth points based at least in part on the correlation, and apply a depth correction to the correlation log.

Statement 18: The system of any previous statements 13 or 14, wherein the openhole log is formed from one or more gamma ray measurements, one or more resistivity measurements, one or more density measurements, one or more neutron measurements, or one or more borehole images.

Statement 19: The system of any previous statements 13, 14, or 18, wherein the correlation log is formed in real-time and wherein the depth-match is performed in real-time based at least in part on the correlation log.

Statement 20: The system of any previous statements 13, 14, 18, or 19, wherein the information handling system is further configured to form a dynamically calibrated depth panel from the relative shift table.

The preceding description provides various embodiments of systems and methods of use which may contain different method steps and alternative combinations of components. It should be understood that, although individual embodiments may be discussed herein, the present disclosure covers all combinations of the disclosed embodiments, including, without limitation, the different component combinations, method step combinations, and properties of the system.

It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the elements that it introduces.

Therefore, the present embodiments are well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Although individual embodiments are discussed, the disclosure covers all combinations of all those embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of the present disclosure. If there is any conflict in the usages of a word or term in this specification and one or more patent(s) or other documents that may be incorporated herein by reference, the definitions that are consistent with this specification should be adopted.

What is claimed is:

1. A method comprising:
   reviewing an openhole log;
   identifying one or more depths within a wellbore for testing from the openhole log;
   disposing a fluid sampling tool into the wellbore;
   creating a correlation log with the fluid sampling tool;
   depth-matching the correlation log to the openhole log to create a relative shift table; and
   moving the fluid sampling tool to the one or more depths within the wellbore based at least in part on the relative shift table.

2. The method of claim 1, wherein the depth-matching is performed with a window-based correlation, an edge-based matching, or a dynamic time warping.

3. The method of claim 2, wherein the window-based correlation, the edge-based matching, or the dynamic time warping are used in a machine learning model to estimate one or more relative shifts that populate the relative shift table.

4. The method of claim 2, wherein the window-based correlation comprises:

overlapping the correlation log and the openhole log;
computing a correlation between the correlation log and the openhole log;
identifying a depth shift to correlate between the correlation log and the openhole log;
interpolating and extrapolating additional depth points based at least in part on the depth shift; and
applying a depth correction to the correlation log.

5. The method of claim 2, wherein the edge-based matching comprises:
identifying one or more significant features in the correlation log and the openhole log;
computing one or more depth shifts based at least in part on the one or more significant features between the correlation log and the openhole log;
computing a correlation between the correlation log and the openhole log using the one or more depth shifts;
interpolating and extrapolating additional depth points based at least in part on the correlation; and
applying a depth correction to the correlation log.

6. The method of claim 1, the openhole log is formed from one or more gamma ray measurements, one or more resistivity measurements, one or more density measurements, one or more neutron measurements, or one or more borehole images.

7. The method of claim 1, wherein the correlation log is formed in real-time.

8. The method of claim 7, wherein the depth-matching is performed in real-time based at least in part on the correlation log.

9. The method of claim 1, further comprising generating the correlation with a gamma ray sensor.

10. The method of claim 1, further comprises aligning one or more significant features on the correlation log to the one or more significant features on the openhole log during the depth-matching.

11. The method of claim 1, further comprising forming a dynamically calibrated depth panel from the relative shift table.

12. The method of claim 11, further comprising landing the fluid sampling tool at the one or more depths when a difference between the dynamically calibrated depth panel and the one or more depths is below a threshold.

13. A system comprising:
a fluid sampling tool disposed in a wellbore to create a correlation log; and
an information handling system connected to the fluid sampling tool comprising at least one processing unit and at least one computer media to:
identify one or more depths within the wellbore for testing using an openhole log;
create the correlation log with the fluid sampling tool;
depth-match the correlation log to the openhole log to create a relative shift table; and
instruct the fluid sampling tool to move to the one or more depths within the wellbore based at least in part on the relative shift table.

14. The system of claim 13, wherein the depth-match is performed with a window-based correlation, an edge-based matching, or a dynamic time warping.

15. The system of claim 14, wherein the window-based correlation, the edge-based matching, or the dynamic time warping are used in a machine learning model to estimate one or more relative shifts that populate the relative shift table.

16. The system of claim 14, wherein the information handling system further utilizes the window-based correlation to:
overlap the correlation log and the openhole log;
compute a correlation between the correlation log and the openhole log;
identify a depth shift to correlate between the correlation log and the openhole log;
interpolate and extrapolate additional depth points based at least in part on the depth shift; and
apply a depth correction to the correlation log.

17. The system of claim 14, wherein the information handling system further utilizes the edge-based matching to:
identify one or more significant features in the correlation log and the openhole log;
compute one or more depth shifts based at least in part on the one or more significant features between the correlation log and the openhole log;
compute a correlation between the correlation log and the openhole log using the one or more depth shifts;
interpolate and extrapolate additional depth points based at least in part on the correlation; and
apply a depth correction to the correlation log.

18. The system of claim 13, wherein the openhole log is formed from one or more gamma ray measurements, one or more resistivity measurements, one or more density measurements, one or more neutron measurements, or one or more borehole images.

19. The system of claim 13, wherein the correlation log is formed in real-time and wherein the depth-match is performed in real-time based at least in part on the correlation log.

20. The system of claim 13, wherein the information handling system further forms a dynamically calibrated depth panel from the relative shift table.

* * * * *